(12) United States Patent
Chacon Quiros et al.

(10) Patent No.: US 11,109,956 B2
(45) Date of Patent: Sep. 7, 2021

(54) GRAVITY SENSITIVE SILICONE BREAST IMPLANTS

(71) Applicant: Establishment Labs S.A., Alajuela (CR)

(72) Inventors: Juan Jose Chacon Quiros, San Jose (CR); Salvador Dada, San Jose (CR); Olivier Tourniaire, San Jose (CR); Luis M. Gutierrez, San Jose (CR)

(73) Assignee: Establishment Labs S.A., Alajuela (CR)

( * ) Notice: Subject to any disclaimer, the term of this patent is extended or adjusted under 35 U.S.C. 154(b) by 0 days.

(21) Appl. No.: 16/027,726

(22) Filed: Jul. 5, 2018

(65) Prior Publication Data

US 2019/0167414 A1    Jun. 6, 2019

Related U.S. Application Data

(63) Continuation of application No. 14/679,788, filed on Apr. 6, 2015, now abandoned.

(60) Provisional application No. 61/975,474, filed on Apr. 4, 2014.

(51) Int. Cl.
    *A61F 2/12*        (2006.01)
    *A61L 27/18*       (2006.01)

(52) U.S. Cl.
    CPC ............... *A61F 2/12* (2013.01); *A61L 27/18* (2013.01); *A61F 2210/0076* (2013.01); *A61F 2230/008* (2013.01); *A61F 2230/0076* (2013.01); *A61L 2400/12* (2013.01)

(58) Field of Classification Search
    USPC ........................................ 623/7, 8
    See application file for complete search history.

(56) References Cited

U.S. PATENT DOCUMENTS

| | | |
|---|---|---|
| 5,104,409 A | 4/1992 | Baker |
| 2010/0226943 A1 | 9/2010 | Brennan et al. |
| 2012/0232652 A1 | 9/2012 | Mora et al. |

OTHER PUBLICATIONS

Therapeutic Goods Administration, "Information regarding tests that have been conducted on silicone gel filled breast implants manufactured by Poly-Implant Prothese (PIP)," downloaded from <https://www.tga.gov.au/media-release/information-regarding-tests-have-been-conducted-silicone-gel-filled-breast-implants-manufactured-poly-implant-prothese-pip> on Nov. 11, 2016. Online publication date of Jan. 12, 2012.

*Primary Examiner* — Yashita Sharma
(74) *Attorney, Agent, or Firm* — Bookoff McAndrews, PLLC

(57) ABSTRACT

A gravity sensitive silicone breast implant is provided which, in various embodiments, has a soft, natural feel and adapts shape after implantation responsive to gravity, according to movements of the patient.

11 Claims, 2 Drawing Sheets

GRAVITY SENSITIVE SILICONE BREAST IMPLANTS

RELATED APPLICATIONS

This application is a continuation of U.S. application Ser. No. 14/679,788, filed on Apr. 6, 2015, which claims the benefit of, and priority to, U.S. Provisional Application No. 61/975,474, filed on Apr. 4, 2014, entitled "Gravity Sensitive Silicone Breast Implants," both of which are incorporated herein by reference in their entireties.

BACKGROUND

Today, the augmentation and reconstruction of the human breast, requiring the use of an implant, has become a fairly common practice in the art of plastic and reconstructive surgery. Typical long-term implantable devices, which are often selected for these procedures, include round or pre-formed anatomically shaped silicone gel-filled implants. However, such implants have a number of drawbacks, including but not limited to a hard, unnatural feel and behavior. Improved implantable devices for breast augmentation are needed.

SUMMARY

The present invention provides, in various embodiments, a gravity sensitive silicone breast implant that has a soft, natural feel and is capable of adapting shape after implantation responsive to gravity, according to movements of the patient.

In one aspect, the invention provides a gravity sensitive silicone breast implant comprising a flexible multilayer shell and a cohesive silicone gel filler with a high elasticity and a low viscosity. The implant is configured to shift its maximum point of projection when subjected to gravity. The flexible multilayer shell of the implant reaches at least 25% elongation at forces of about 1.4 N to about 1.9 N and at least 50% elongation at forces of about 1.8 N to about 2.2 N when tested in accordance with ASTM D412. The silicone gel filler reaches about 2 mm to about 29 mm protrusion in a cone cohesion test and will not detach from the cone when tested in accordance with ASTM F703.

In some embodiments, the flexible multilayer shell has a nano-textured outer surface. In other embodiments, the flexible multilayer shell has a micro-textured outer surface.

In some embodiments, the flexible multilayer shell has a thickness of about 0.008 in to about 0.030 in.

In some embodiments, the flexible multilayer shell includes at least one low diffusion barrier layer.

In some embodiments, the low diffusion barrier layer comprises a polysiloxane backbone having at least 10 mole percent of a pendant chemical group that retards permeation of silicone gel through the low diffusion barrier layer.

In some embodiments, the low diffusion barrier layer comprises a polydimethylsiloxane backbone having at least 10 mole percent of a pendant chemical group comprising at least one of a phenyl group and a fluorine group.

In some embodiments, the low diffusion barrier layer comprises a polydimethylsiloxane backbone having at least 10 mole percent of a pendant chemical group comprising at least one of a diphenyl group, a methylphenyl group, a trifluoropropyl group, and mixtures thereof.

In some embodiments, the low diffusion barrier layer has a color.

In some embodiments, the gravity sensitive silicone breast implant has a round base.

In alternative embodiments, the gravity sensitive silicone breast implant has an oval base.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of the preferred embodiments of the application, will be better understood when read in conjunction with the appended drawings. For the purposes of illustrating the implants of the present application, there are shown in the drawings preferred embodiments. It should be understood, however, that the application is not limited to the precise arrangements and instrumentalities shown. In the drawings.

DETAILED DESCRIPTION

Figure 1:
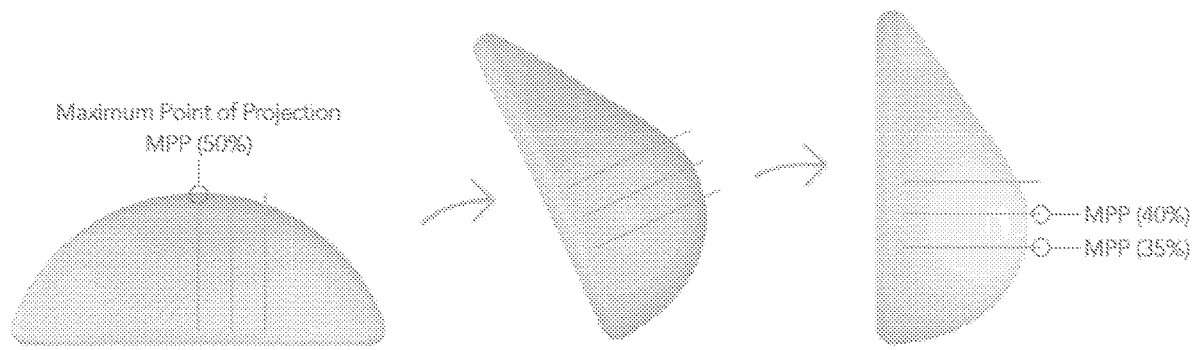
FIG. 1 shows the variation in the shape and the shifting of the maximum point of projection from the apex of a gravity sensitive silicone breast implant of the present invention, according to some embodiments.

Typical silicone gel-filled breast implants are mammary augmentation devices constructed of a shell comprising successive cross-linked layers of silicone elastomer, which gives the implants their elasticity and integrity. All silicone gel-filled implants are composed, at least, of the above-mentioned shell, a silicone patch, and silicone gel fill.

The objective of most of the surgical procedures performed to increase breast size, including all reconstruction procedures, is to recreate the feel, look and behavior of the natural breast tissue. In the past, this objective has been addressed by means of creating preformed anatomical implants to reproduce the natural shape of the human breast. Nevertheless, this approach has created problems of its own that in many aspects deter from the original intention.

Preformed anatomical implants work on the basis of retaining at all times after implantation a predefined form that is viewed as anatomically correct for the breasts. This is achieved by means of creating an implant that retains its form by utilizing a highly cohesive filling gel with a high viscosity and a low elasticity, together with a shell made to maintain its form at all times. The aesthetic result is very good, as long as the patient is upright, motionless, and as long as the breasts are not touched. Preformed anatomical implants are hard and, once implanted, maintain their form independently of the position or action taken by the patient. These implants do not resemble the human tissue in movement or when touched. There is no natural interaction between the breast tissue and the silicone breast implant.

Patients and their partners typically complain about how unnatural those implants feel and behave after implantation.

Additionally, traditional anatomical implants suffer from complications endemic to their kind. Since they are preformed to have a teardrop-like form, they need to be implanted in a very precise position, and no deviation, movement or rotation is acceptable because it would show as a deformation of the breast. Rotation and misplacement of anatomical breast implants is very common and the only existing solution is re-operation.

In an effort to avoid rotation and movement of preformed anatomical breast implants, manufacturing companies have opted to give these implants very rough and aggressive surface textures, with the purpose of making them adhere to the surrounding tissue, or at least create sufficient friction to avoid slippage. This approach has proven successful to some degree, but has created a new set of problems.

Very aggressive surface textures on the outer shell of breast implants have been identified as the cause of newer complications originating in the shear forces causing irritation, which can develop into late seromas and double capsules, leading to the necessity of reoperation and additional procedures to attain a healthy and acceptable aesthetic outcome.

The present invention provides, in various embodiments, an alternative to anatomical preformed breast implants that eliminates the above-described problems associated with their use, but maintains their positive aesthetic features. In various embodiments, the invention provides a silicone breast implant: without an aggressively textured outer surface; with a consistency similar to human tissue; which replicates and allows the natural movements of the body; and/or which eliminates or greatly diminishes the problem of implant rotation.

The present invention provides, in various embodiments, a gel-filled implant consisting of an internal cohesive silicone gel and a flexible silicone shell enclosing the gel. Once implanted, the implant will shift its point of maximum projection according to the movements of the patient, driven only by the force of gravity. This shifting enables the implant resemble the movement of natural breast tissue to obtain a real anatomical result. The implant has a sensation to touch soft enough to resemble the sensation of breast tissue. The implant of the present invention provides an improved, closer reproduction of natural breast tissue according to standard visual and tactile perceptions.

Figure 2:
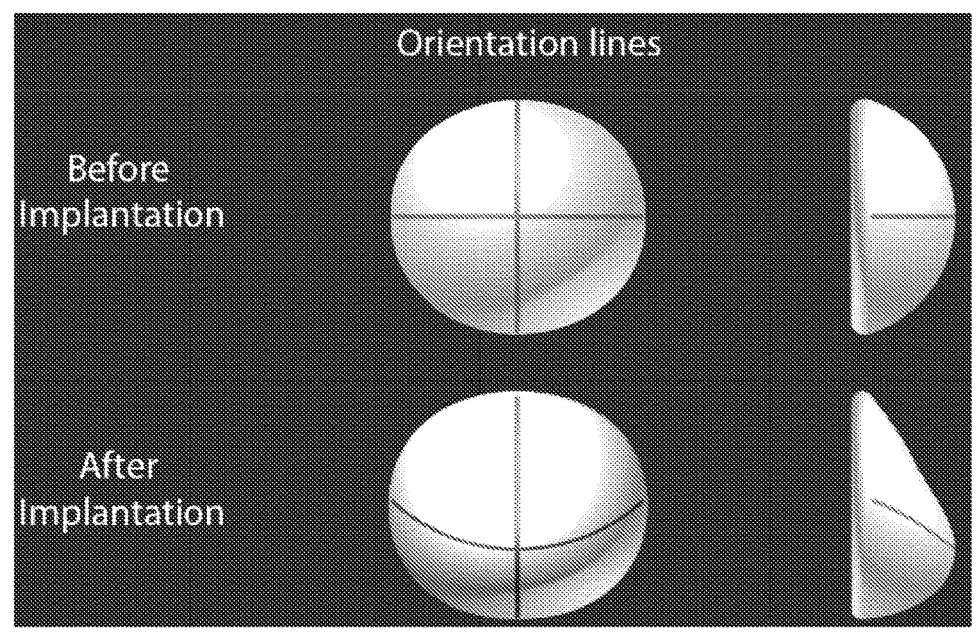
FIG. 2 shows the variation in the shape and the shifting of the maximum point of projection from the apex of the breast implant before implantation and after implantation when the patient is standing up, according to some embodiments.

The implant of the present invention advantageously adapts shape after implantation to give the natural look of traditional preformed anatomical implants, without the complications associated with rotation, implant hardness, and/or aggressive textures. As shown, for example, in FIGS. 1 and 2, the implant of the present invention, when subjected to gravity, will advantageously shift the maximum point of projection to the lower pole of the implant when the patient is in a standing position. When the patient lays flat on her back, the implant will react as a natural breast and the maximum point of projection will move closer to the middle point of her breast.

Figure 3:
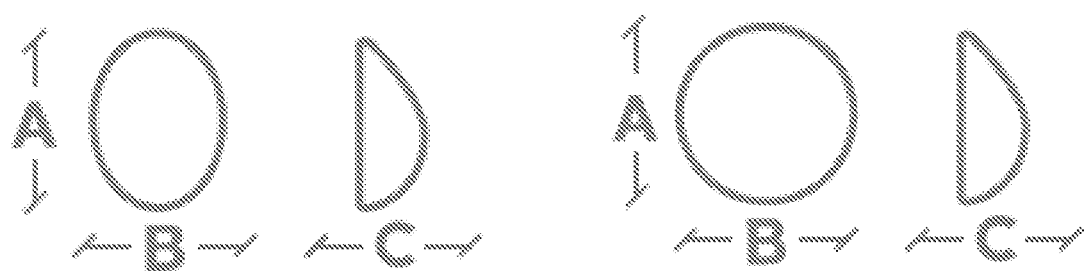
FIG. 3 shows two possible base variations of the invention, at left, where A and B are different measures (oval base) and, at right, where A and B are equal measures (round base).

As shown, for example, in FIG. 3, the implant can have a round or oval base where all four quadrants are equivalent. When employing a round base this condition allows the placement of the implant using the same techniques employed for the placement of non-anatomical breast implants, which makes for a simpler procedure. Even though the result resembles an anatomically correct breast, the breast implant of the present invention having a round base can rotate in its vertical axis without impairing that result.

When employing an oval base, the surgeon may choose whether the physical characteristics of the patient call for the placement of the implant in a vertical alignment of the longest or shortest diameter of the implant with the patient's height. Due to the adaptation of the implant according to the gravity pull, the aesthetic result in case of a rotation would not be seriously affected, or would not be noticeable to a large degree, minimizing the possible complication. Since the gravity vector is equal in rotated or non-rotated implants, the maximum point of projection would tend to be localized in the same desired area.

Due to the described characteristics of the implants of the present invention that eliminate or diminish the incidence of rotation as a possible complication in breast augmentation procedures, the need for aggressive textures on the outer side of the implant shell is advantageously eliminated or diminished. Accordingly, implants of the present invention can have a smooth (e.g., nano-textured or micro-textured) outer surface throughout, thus negating the additional range of complications that can develop from the use of aggressive textures.

In some embodiments, the shell of the implant of the present invention is a multilayer structure with at least one low diffusion barrier layer included with (inside, outside, or nestled between) a plurality of standard silicone elastomer layers. The barrier layer(s) can be, for example, made of silicone elastomer comprising a polysiloxane backbone and having a minimum mole percentage of 10% of a substituted or pendant chemical group that retards permeation of silicone gel through the layer. In some embodiments, the silicone elastomer present in the barrier layer(s) is a polydimethylsiloxane and the pendant chemical group is a phenyl group (e.g., a diphenyl group or a methylphenyl group), a fluorine group (e.g., a trifluoropropyl group), or a mixture thereof. In some embodiments, the shell may comprise colored barrier layer(s) as described, for example, in U.S. patent application Ser. No. 13/412,221, which is incorporated herein by reference in its entirety.

Various systems and methods can be used for constructing a silicone implant elastomeric shell and they are contemplated in this invention. In some embodiments, the step of forming the shell comprises coating a mold with a liquid elastomer; the shell may be formed by dipping, spraying, pouring, blowing or rotational molding, using a suitably shaped mold, coated with dispersion of a silicone elastomer and a solvent, allowing the solvent to volatize, and allowing the elastomer to cure.

In some embodiments, the implant of the present invention achieves a pliable sensation resembling breast tissue and the possibility of varying its shape from the use of an outer silicone elastomer shell that is able to stretch with the application of small forces which may come from the movement of the gel or the application of force by hand. This flexibility can be measured and demonstrated by calculating the stress of the shell at 25% and 50% elongation on the apex section of the shell. Existing silicone shelled breast implants have shells that require average forces from 2 to 3 Newtons (N) or higher when tested for stress at 25% elongation, and average forces from 2.7 to 3.5 N or higher when tested for stress at 50% elongation, measured according to ASTM D412 (Standard Test Methods for Vulcanized Rubber and Thermoplastic Elastomers—Tension; see, e.g., www.astm.org/Standards/D412.htm). In contrast, in various embodiments, implants of the present invention comprise an outer shell having an average thickness ranging from 0.008 to 0.030 inches, and requiring forces at the apex from about 1.4 to about 1.9 N when tested for stress at 25% elongation and from about 1.8 to about 2.2 N when tested for stress at 50% elongation, measured according to ASTM D412.

In some embodiments of the present invention, movement or conformation of the implant mass according to the gravity vector is obtained by using a cohesive silicone gel filler with a high elasticity and a low viscosity. The desired cohesiveness characteristics are preferably achieved using a gel that will attain a value in the range of 2 to 29 mm protrusion in the cone cohesion test and that will not detach from the cone, according to the test previewed in ISO 14607:2009 (Non-active surgical implants—Mammary implants—Particular requirements; see, e.g., www.iso.org/iso/home/store/catalogue_tc/catalogue_detail.htm?csnumber=38760) and ASTM F703 (Standard Specification for Implantable Breast Prostheses; see, e.g., http://www.astm.org/Standards/F703.htm).

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

The invention claimed is:

1. A gravity sensitive silicone breast implant, comprising a flexible multilayer shell and a cohesive silicone gel filler with a high elasticity and a low viscosity, the breast implant being configured to shift its maximum point of projection when subjected to gravity, wherein the flexible multilayer shell reaches at least 25% elongation at forces of about 1.4 N to about 1.9 N and at least 50% elongation at forces of about 1.8 N to about 2.2 N when tested in accordance with ASTM D412, and wherein the silicone gel filler reaches about 2 mm to about 29 mm protrusion in a cone cohesion test without detaching when tested in accordance with ASTM F703.

2. The gravity sensitive silicone breast implant of claim 1, wherein the flexible multilayer shell has nanoscale features on an outer surface of the shell.

3. The gravity sensitive silicone breast implant of claim 1, wherein the flexible multilayer shell has microscale features on an outer surface of the shell.

4. The gravity sensitive silicone breast implant of claim 1, wherein the flexible multilayer shell has a thickness of about 0.008 in to about 0.030 in.

5. The gravity sensitive silicone breast implant of claim 1, wherein the flexible multilayer shell includes at least one low diffusion barrier layer.

6. The gravity sensitive silicone breast implant of claim 5, wherein the low diffusion barrier layer comprises a polysiloxane backbone having at least 10 mole percent of a pendant chemical group that retards permeation of silicone gel through the low diffusion barrier layer.

7. The gravity sensitive silicone breast implant of claim 5, wherein the low diffusion barrier layer comprises a polydimethylsiloxane backbone having at least 10 mole percent of a pendant chemical group comprising at least one of a phenyl group and a fluorine group.

8. The gravity sensitive silicone breast implant of claim 5, wherein the low diffusion barrier layer comprises a polydimethylsiloxane backbone having at least 10 mole percent of a pendant chemical group comprising at least one of a diphenyl group, a methylphenyl group, a trifluoropropyl group, or a mixture thereof.

9. The gravity sensitive silicone breast implant of claim 5, wherein the low diffusion barrier layer has a color.

10. The gravity sensitive silicone breast implant of claim 1, wherein the implant has a round base.

11. The gravity sensitive silicone breast implant of claim 1, wherein the implant has an oval base.

\* \* \* \* \*